(12) United States Patent
DiZio et al.

(10) Patent No.: US 10,376,473 B2
(45) Date of Patent: *Aug. 13, 2019

(54) TRANSDERMAL ADHESIVE COMPOSITIONS, DEVICES, AND METHODS

(71) Applicant: 3M INNOVATIVE PROPERTIES COMPANY, St. Paul, MN (US)

(72) Inventors: James P. DiZio, St. Paul, MN (US); Elizabeth E. Johnson, Afton, MN (US); Zheng Z. Wu, Santa Clara, CA (US); Amy Preszler Prince, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/042,361

(22) Filed: Jul. 23, 2018

(65) Prior Publication Data

US 2018/0325838 A1 Nov. 15, 2018

Related U.S. Application Data

(60) Continuation of application No. 15/168,270, filed on May 31, 2016, now Pat. No. 10,034,840, which is a division of application No. 13/811,343, filed as application No. PCT/US2011/044522 on Jul. 19, 2011, now Pat. No. 9,375,510.

(60) Provisional application No. 61/366,358, filed on Jul. 21, 2010.

(51) Int. Cl.

| A61K 9/70 | (2006.01) |
|---|---|
| A61K 31/165 | (2006.01) |
| C09J 4/06 | (2006.01) |
| C09J 133/08 | (2006.01) |
| C09J 133/10 | (2006.01) |
| A61K 31/27 | (2006.01) |
| A61L 24/06 | (2006.01) |
| C08F 220/18 | (2006.01) |

(52) U.S. Cl.
CPC .......... *A61K 9/7061* (2013.01); *A61K 31/165* (2013.01); *A61K 31/27* (2013.01); *A61L 24/06* (2013.01); *C08F 220/18* (2013.01); *C09J 4/06* (2013.01); *C09J 133/08* (2013.01); *C09J 133/10* (2013.01); *C08F 2220/1858* (2013.01)

(58) Field of Classification Search
CPC ............ C08F 2220/1858; C08F 218/08; C08F 220/56; C08F 220/18; A61K 31/165; A61K 31/27; A61K 9/7061; A61L 24/06; C09J 133/08; C09J 133/10; C09J 4/06
See application file for complete search history.

(56) References Cited

U.S. PATENT DOCUMENTS

| 2,884,126 | A | 4/1959 | Ulrich | |
|---|---|---|---|---|
| 4,196,111 | A | 4/1980 | Gomez | |
| 4,737,577 | A | 4/1988 | Brown | |
| 5,376,703 | A | 12/1994 | Noelken | |
| 5,698,217 | A | 12/1997 | Wilking | |
| 5,990,229 | A * | 11/1999 | Hille | A61K 8/0208 |
| | | | | 524/555 |
| 6,335,031 | B1 | 1/2002 | Asmussen | |
| 6,592,860 | B1 | 7/2003 | Gerdon | |
| 7,030,199 | B1 | 4/2006 | Chmelir | |
| 7,097,853 | B1 | 8/2006 | Garbe | |
| 7,332,540 | B2 | 2/2008 | Bamborough | |
| 8,039,528 | B2 | 10/2011 | Zhu | |
| 9,375,510 | B2 * | 6/2016 | DiZio | A61K 9/7061 |
| 10,034,840 | B2 * | 7/2018 | Dizio | A61K 9/7061 |
| 2002/0119187 | A1 | 8/2002 | Cantor | |
| 2004/0057986 | A1 | 3/2004 | Merrigan et al. | |
| 2004/0266965 | A1 | 12/2004 | Holguin | |
| 2007/0098766 | A1 | 5/2007 | Kawamura et al. | |
| 2007/0128263 | A1 | 6/2007 | Gargiulo | |
| 2007/0148218 | A1 | 6/2007 | Gordon | |
| 2008/0206339 | A1 | 8/2008 | Omidian | |
| 2008/0269449 | A1 | 10/2008 | Chattopadhyay | |
| 2009/0018274 | A1 * | 1/2009 | Zhu | C08F 6/006 |
| | | | | 525/387 |

(Continued)

FOREIGN PATENT DOCUMENTS

| CN | 101302275 | 11/2008 |
|---|---|---|
| EP | 0818470 | 1/1998 |
| JP | H05-131022 | 5/1993 |

(Continued)

OTHER PUBLICATIONS

Li et al (Journal of Controlled Release, 2002, vol. 82, pp. 1-16) (Year: 2002).*
"*Textbook of Polymer Science*", F.W. Billmeyer, Wiley Interscience, Second Edition (1971), pp. 84 and 85.
PCT International Search Report from PCT/US2011/044522—3M Case # 66764WO003.
Araujo, P.H.H. et al.; "Techniques for Reducing Residual Monomer Content in Polymers: A Review"; Polymer Engineering and Science; vol. 42, No. 7; 2002; pp. 1442-1468.
Odian, G.; Principles of Polymerization Third Edition; 1991 p. 241-242.

(Continued)

*Primary Examiner* — Mark V Stevens
(74) *Attorney, Agent, or Firm* — Eric E. Silverman

(57) ABSTRACT

A stable transdermal adhesive composition comprising: an adhesive comprising a washed polymerization reaction product of at least two ethylenically unsaturated monomers; and at least one pharmaceutically active compound which is susceptible to oxidative degradation; wherein the at least two ethylenically unsaturated monomers, if present in the adhesive as unreacted monomers, are present at a level of less than 200 ppm of total unreacted monomer, based upon the total weight of the adhesive, methods of making the composition, a transdermal drug delivery device using the composition, methods of making the device, and methods of delivery the pharmaceutically active compound are provided.

21 Claims, No Drawings

(56) References Cited

U.S. PATENT DOCUMENTS

2009/0297591 A1* 12/2009 Chiang ............... A61K 9/7061
424/449
2010/0087768 A1 4/2010 Forlano et al.

FOREIGN PATENT DOCUMENTS

| | | |
|---|---|---|
| JP | 7331217 | 12/1995 |
| JP | 2000-053564 | 2/2000 |
| JP | 2002212221 | 7/2002 |
| JP | 2004083619 | 3/2004 |
| JP | 2006328264 | 12/2006 |
| KR | 10-2008-0006961 | 1/2008 |
| WO | WO 96/30001 | 10/1996 |
| WO | WO 99/34782 | 7/1999 |
| WO | WO 2001/30316 | 5/2001 |
| WO | WO 2004/003024 | 1/2004 |
| WO | WO 2004/022609 | 3/2004 |
| WO | WO 2005/049090 | 6/2005 |
| WO | WO 2006/044590 | 4/2006 |

OTHER PUBLICATIONS

Patel, N.N. et al.; "Critical review: Significance of Force degradation study with respect to current Pharmaceutical Scenario"; Asian J. Research Chem; vol. 6, No. 3; 2013; pp. 286-296.

* cited by examiner

TRANSDERMAL ADHESIVE COMPOSITIONS, DEVICES, AND METHODS

CROSS REFERENCE TO RELATED APPLICATIONS

This application is a continuation of U.S. patent application Ser. No. 15/168,270, filed May 31, 2016, which is a division of U.S. patent application Ser. No. 13/811,342, filed Jan. 21, 2013, now U.S. Pat. No. 9,375,510, which is a national stage filing under 35 U.S.C. 371 of PCT/US2011/044522, filed Jul. 19, 2011, which claims the benefit of U.S. Provisional Application No. 61/366,358, filed Jul. 21, 2010, the disclosure of which is incorporated by reference in their entirety herein.

BACKGROUND

Transdermal administration of a drug can provide a number of possible advantages, such as avoidance of first-pass metabolism, avoidance of gastro-intestinal irritation, sustained release, and improved patient compliance with treatment regimens. Transdermal drug delivery devices used for this purpose are typically designed to deliver a therapeutically effective amount of drug across the skin of a subject. The drug is normally incorporated into a carrier, such as a liquid, gel, solid matrix, or pressure sensitive adhesive. Reservoir type devices may include a membrane that controls the rate of drug release to the skin, while other devices may have a drug dispersed or dissolved in a matrix such as a pressure sensitive adhesive.

Drug dosages have been directly incorporated into the adhesive portion of transdermal patches where the adhesive is used to secure the patch to skin. Efforts to remove residual monomer components and the like from adhesives for contacting skin have been reported with the aim of reducing skin irritation, improving adhesive properties, such as adhesion, and/or reducing unpleasant odors.

However, there continues to be an interest in and a need for improved transdermal drug delivery devices and adhesive compositions used therein.

SUMMARY OF THE INVENTION

It has now been found that pharmaceutically active compounds which are subject to oxidative degradation can be incorporated into certain adhesive compositions, providing compositions with enhanced stability. Moreover, it has now been found that pharmaceutically active compounds which are subject to oxidative degradation, and therefore require an antioxidant to provide sufficient stability in a carrier, can be incorporated into certain adhesive compositions without the need for an antioxidant.

Accordingly, in one embodiment there is provided a transdermal adhesive composition comprising:

an adhesive comprising a washed polymerization reaction product of at least two ethylenically unsaturated monomers; and at least one pharmaceutically active compound which is susceptible to oxidative degradation;

wherein the at least two ethylenically unsaturated monomers, if present in the adhesive as unreacted monomers, are present at a level of less than 200 ppm of total unreacted monomer, based upon the total weight of the adhesive; and wherein any free radical initiator, if present in the adhesive, is present at a level of less than 20 ppm, based upon the total weight of the adhesive.

In another embodiment, there is provided a transdermal adhesive composition comprising:

an adhesive comprising a washed polymerization reaction product of at least two ethylenically unsaturated monomers; and (S)—N-ethyl-N-methyl-3-[1-(dimethylamino)ethyl]phenyl carbamate or a pharmaceutically acceptable salt thereof;

wherein the at least two ethylenically unsaturated monomers, if present in the adhesive as unreacted monomers, are present at a level of less than 200 ppm of total unreacted monomer, based upon the total weight of the adhesive.

In another embodiment, there is provided a transdermal drug delivery device comprising:

a transdermal adhesive composition comprising:

an adhesive comprising a washed polymerization reaction product of at least two ethylenically unsaturated monomers; and at least one pharmaceutically active compound which is susceptible to oxidative degradation;

wherein the at least two ethylenically unsaturated monomers, if present in the adhesive as unreacted monomers, are present at a level of less than 200 ppm of total unreacted monomer, based upon the total weight of the adhesive; and a backing sheet coated with the transdermal adhesive composition, wherein the transdermal adhesive composition coating covers at least a portion of a major surface of the backing sheet.

In another embodiment, there is provided a method of making a stable transdermal adhesive composition comprising:

providing a polymerization reaction product of at least two ethylenically unsaturated monomers; and wherein the polymerization reaction product is dissolved and/or dispersed in a first liquid;

separating at least a portion of the polymerization reaction product from the first liquid to provide a first washed polymerization reaction product;

dissolving or dispersing the first washed polymerization reaction product in a second liquid;

separating at least a portion of the first washed polymerization reaction product from the second liquid to provide a second washed polymerization reaction product;

wherein the at least two ethylenically unsaturated monomers, if present in the second washed polymerization reaction product, are present at a level of less than 200 ppm of total unreacted monomer, based upon the total weight of the second washed polymerization reaction product; and combining the second washed polymerization reaction product with at least one pharmaceutically active compound which is susceptible to oxidative degradation to form a stable transdermal adhesive composition.

In another embodiment, there is provided a method of making a stable transdermal drug delivery device comprising:

providing a transdermal adhesive composition according to any one of the above composition embodiments or any embodiment thereof described herein or a transdermal adhesive composition made according to the above method embodiment or any embodiment thereof described herein; and coating a backing sheet with the transdermal adhesive composition, wherein the transdermal adhesive composition coating covers at least a portion of a major surface of the backing sheet.

In a further embodiment, there is provided a method of delivering a pharmaceutically active compound to a mammal comprising the steps of:

providing a transdermal adhesive composition according to any one of the above composition embodiments or any embodiment thereof described herein or a transdermal adhesive composition made according to the above method embodiment or any embodiment thereof described herein or a device according to the above device embodiment or any embodiment thereof described herein or a device made according to the above method of making a device embodiment or any embodiment thereof described herein;

positioning the transdermal adhesive composition on the skin of the mammal; and allowing the composition to remain on the skin for a time sufficient to permit systemic delivery of the pharmaceutically active compound;

wherein the pharmaceutically active compound is susceptible to oxidative degradation.

DEFINITIONS

The following terms are used herein according to the following definitions.

As used herein, "washing" or "washed" refers to a polymerization reaction product which has been dissolved or dispersed in a liquid, such as an organic solvent, and then separated from the liquid, such that the level of unreacted monomer is reduced, for example, to less than 200 ppm of total unreacted monomer, based upon the total weight of the washed polymerization reaction product or the adhesive comprising the washed polymerization reaction product. For certain embodiments, preferably the level of unreacted monomer is reduced to less than 100 ppm, even more preferably less than 50 ppm of total unreacted monomer.

"Stable" means both chemically and physically stable. As used herein "physically stable" compositions are those that do not significantly change due to substantial precipitation, crystallization, phase separation, and the like, from their original condition during storage at 25° C. for at least 3 months, and preferably for at least 6 months. As used herein, "chemically stable" compositions retain an average of at least 98% of the pharmaceutically active compound after aging for 2 months at 60° C. in ambient humidity or degrade the pharmaceutically active compound, forming less than 2 percent by weight degradation products based upon the total starting weight of the pharmaceutically active compound. For certain embodiments, preferably stable compositions retain an average of at least 99% of the pharmaceutically active compound after aging for 2 months at 60° C. in ambient humidity or degrade the pharmaceutically active compound, forming less than 1 percent by weight degradation products based upon the total starting weight of the pharmaceutically active compound. The level of pharmaceutically active compound or degradation product thereof is preferably determined using gas chromatography or high performance liquid chromatography using appropriate standards and controls.

As used herein, "susceptible to oxidative degradation" refers to pharmaceutically active compounds which may be combined with an antioxidant when made into a drug product to keep the active compound stable during the life of the drug product.

As used herein, "essentially free of any added antioxidant" refers to a transdermal adhesive composition to which no antioxidant has been added for the purpose of preventing a pharmaceutically active compound susceptible to oxidative degradation from forming total drug impurities in excess of 2% within two years at room temperature or 2 months at 60° C. with ambient humidity. For certain embodiments, preferably less than 0.1%, more preferably less than 0.05%, most preferably less than 0.01% antioxidant is present in the transdermal adhesive composition which is "essentially free of any added antioxidant."

"Subject" and "patient" includes humans, sheep, horses, cattle, pigs, dogs, cats, rats, mice, or other mammals.

The terms "comprises" and variations thereof do not have a limiting meaning where these terms appear in the description and claims.

As used herein, "a," "an," "the," "at least one," and "one or more" are used interchangeably. The term "and/or" means one or all of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The present invention provides stable transdermal adhesive compositions with enhanced stability, in certain embodiments, preferably without a need for adding an antioxidant or with a reduced level of antioxidant when incorporating pharmaceutically active compounds susceptible to oxidative degradation.

FDA Guidance Q3B(R2): Impurities in New Drug Products indicates that for a drug product to be considered stable, total drug impurities must not exceed 2%. In order to sufficiently limit the formation of drug impurities associated with oxidative degradation, antioxidants have been added to drug compositions, thereby achieving the required level of stability. For example, U.S. Pat. No. 6,335,031 reports compositions, containing a cholinesterase inhibitor ((S)—N-ethyl-3-[(1-dimethylamino)ethyl]-N-methylphenyl carbamate) with 0.1% tocopherol (antioxidant), with 1.3% degradation products after 2 months at 60° C., but with 4.46% degradation products without the antioxidant.

Applicants have now found stable transdermal adhesive compositions comprising an adhesive comprising a washed polymerization reaction product of at least two ethylenically unsaturated monomers, and at least one pharmaceutically active compound which is susceptible to oxidative degradation. The polymerization reaction product is washed such that the at least two ethylenically unsaturated monomers, if present in the adhesive as unreacted monomers after washing, are reduce to at a level of less than 200 ppm of total unreacted monomer, based upon the total weight of the adhesive. For certain embodiments, preferably such compositions are stable without the need to add any antioxidant. For certain embodiments, such compositions are stable even when an amount of antioxidant is used which is less than, for example, half the amount of antioxidant needed when an unwashed polymerization reaction product is used. For certain of these embodiments, the amount of antioxidant is less than 25 percent or less than 10 percent of the amount of antioxidant needed when an unwashed polymerization reaction product is used.

The adhesive is preferably a pressure sensitive adhesive, and, except for the washing described herein, the polymerization reaction product which the adhesive comprises can be made by free radical polymerization of the ethylenically unsaturated monomers using known radical polymerization methods. See for example, U.S. Pat. No. RE 24,906 (Ulrich). Thermally or photochemically activated free radical-forming initiators may be used to carry out the polymerization reaction. Preferably, such initiators are other than peroxide initiators. Suitable thermally activated initiators include azo compounds such as 2,2'-azobis(isobutyronitrile), 2,2'-azobis(2,4-dimethylvaleronitrile), and the like. Suitable photochemically activated initiators include, for example, benzoin ethyl ether, 2,2-dimethoxy-2-phenylacetophenone, and the like. The polymerization reaction can be conveniently carried out in a solvent using conventional free radical solution polymerization methods.

Such polymerization reactions result in the formation of a polymer along with some level of unreacted monomers and initiator. The present washed polymerization reaction product has significantly reduced levels of both unreacted monomers and initiator. While the reduced levels of unreacted monomers and initiator indicate that the polymerization reaction product is sufficiently washed to provide the stable transdermal adhesive composition, the reason for the surprising degree of stability so obtained is not known. Moreover, this result is achieved without using purification steps involving the addition of an oxidizing agent and a reducing agent which react with one another to generate free radicals which can initiate further polymerization of the unreacted monomer included with the polymerization reaction product.

For certain embodiments, including any one of the above embodiments, preferably the at least two ethylenically unsaturated monomers, if present in the adhesive, are present at a level of less than 100 ppm of total unreacted monomer, based upon the total weight of the adhesive, more preferably less than 50 ppm or below the detectable level. In addition, when an acrylamide or methacrylamide is used to prepare the polymerization reaction product, these unreacted monomers, if present in the adhesive, are present at a level of less than 30 ppm based upon the total weight of the adhesive, preferably less than 16 ppm or even less than 5 ppm.

For certain embodiments, including any one of the above embodiments, preferably any free radical initiator, if present in the adhesive, is present at a level of less than 20 ppm, based upon the total weight of the adhesive comprising the washed polymerization reaction product. For certain of these embodiments, preferably any free radical initiator, if present in the adhesive, is present at a level of less than 10 ppm, more preferably less than 5 ppm.

For certain embodiments, including any one of the above embodiments, the at least two ethylenically unsaturated monomers comprise an ethylenically unsaturated group selected from the group consisting of acryloyl, methacryloyl, vinyl, and a combination thereof.

For certain embodiments, including any one of the above embodiments, the adhesive comprises the copolymerization product of at least one first monomer selected from the group consisting of $C_4$ to $C_{12}$ alkyl acrylate monomers, $C_4$ to $C_{12}$ alkyl methacrylate monomers, and combinations thereof; and at least one second monomer selected from the group consisting of acrylamide, N,N-diethylacrylamide, methacrylamide, vinyl acetate, vinyl alcohol, N-vinyl-2-pyrrolidone, 2-hydroxyethyl acrylate, 2-hydroxyethyl methacrylate, hydroxpropyl acrylate, glyceryl acrylate, 2-ethoxyethyl acrylate, 2-ethoxyethoxyethyl acrylate, tetrahydrofurfuryl acrylate, acrylic acid, methacrylic acid, pyrrolidonylethyl acrylate, 2-carboxyethyl acrylate, and combinations thereof. For certain of these embodiments, preferably the at least one first monomer is selected from the group consisting of isooctyl acrylate, 2-ethylhexyl acrylate, cyclohexyl acrylate, 2-methylbutyl acrylate, butyl acrylate, and combinations thereof. For certain of these embodiments, preferably the at least one second monomer is selected from the group consisting of acrylamide, vinyl acetate, and a combination thereof. The amount of the at least one first monomer, is typically between about 40% and about 98%, more typically between about 60% and about 95%, and most preferably between about 70% and about 90% by weight of the resulting copolymer composition. The amount of the at least one second monomer is typically between about 2% and about 60%, more typically between about 3% and about 40%, and most preferably between about 4% and about 30% by weight of the copolymer composition. The copolymers comprising the pressure sensitive adhesive may optionally further comprise other radically polymerizable monomers that are well known in the art. The copolymers comprising the pressure sensitive adhesive may optionally further comprise a substantially linear macromonomer copolymerizable with the other monomers. Suitable macromonomers include polymethylmethacrylate, styrene/acrylonitrile copolymer, polyether, and polystyrene macromonomers.

For certain embodiments, including any one of the above embodiments, the adhesive comprises the co-polymerization product of isooctyl acrylate, acrylamide, and vinyl acetate. For certain of these embodiments, the isooctylacrylate is 70-80%, the acrylamide is 3-7%, and the vinyl acetate is 15-25% of the copolymerization product on a weight basis. For certain of these embodiments, the isooctyl acrylate/acrylamide/vinyl acetate weight ratio is 75/5/20.

Additional examples of adhesives which may be used in the present compositions, methods, and devices include copolymers of isooctyl acrylate/acrylamide (for example, about 93/7 weight ratio); copolymers of ethylhexyl acrylate, butyl acrylate, and vinyl acetate; DUROTAK 87-2353, 387-2353, 387-2051, and 387-2052 (National Starch and Chemical Company, Zutphen, Holland); PLASTOID B (Rohm, Darmstadt, Germany); and EUDRAGIT E 100 (Rohm, Darmstadt, Germany).

For certain embodiments, including any one of the above embodiments, pharmaceutically active compounds which are susceptible to oxidative degradation are those which when not used in the present compositions may be combined with an antioxidant in order to prevent total drug impurities from exceed 2% within two years at room temperature or 2 months at 60° C. with ambient humidity. For certain of these embodiments, the pharmaceutically active compound includes at least one group selected from the group consisting of tertiary amino, secondary amino, benzylic hydrogen-containing group, and combinations thereof. A benzylic hydrogen-containing group includes a hydrogen atom bonded to a carbon atom, the carbon atom being bonded directly to a phenyl group. For certain embodiments, the pharmaceutically active compound includes at least one tertiary amino group. Pharmaceutically active compounds which contain at least one of these groups are subject to oxidative degradation and may be used in the compositions, devices, and methods described herein without the addition of an antioxidant or with the addition of less than 50%, less than 25%, or less than 10% the amount of antioxidant needed to achieve an equivalent degree of stability when used in an unwashed adhesive. For certain of these embodiments, the pharmaceutically active compound is selected from the group consisting of: rivastigmine ((S)—N-ethyl-N-methyl-3-[1-(dimethylamino)ethyl]phenyl carbamate), buprenorphine, etidocaine, ropivacaine, clonidine, lidocaine, letrozole, fentanyl, indapamide, apomorphine, propylnorapomorphine, salbutamol, lisuride, dihydroergotamine, pergolide, terguride, proterguride, propranolol, imipramine, guanethidine, cyproheptadine and a pharmaceutically acceptable salt of any one of the preceding compounds. For certain of these embodiments, preferably the pharmaceutically active compound is selected from the group consisting of: rivastigmine, lidocaine, buprenorphine, etidocaine, ropivacaine, fentanyl, clonidine, and a pharmaceutically acceptable salt of any one of the preceding compounds. For certain of these embodiments, most preferably the pharmaceutically active compound is rivastigmine ((S)—N-ethyl-N-methyl-3-[1-(dimethylamino)ethyl] phenyl carbamate) or a pharmaceutically acceptable salt thereof.

As indicated above, the present transdermal adhesive compositions have been found to be stable without the need for adding any antioxidant. Accordingly, for certain embodiments, including any one of the above embodiments, the composition is essentially free of any added antioxidant. Examples of such antioxidants include butylated hydroxyanisole (BHA), butylated hydroxytoluene (BHT), tertiary butyl hydroquinone (TBHQ), propyl gallate, ascorbic acid and esters thereof, e.g., ascorbyl palmitate, tocopherol and esters thereof, e.g., tocopherol acetate, and including isomers thereof, polyphenolic antioxidants, flavonoids, isoflavonoids, neoflavonoids, flavinoids, isoflavinoids, neoflavinoids, quercetin, rutin, epicatechins, resveratrol, thioglycerol, thioglycolic acid, thiourea, acetylcysteine, sodium bisulfate, sodium sulfite, sodium metabisulfite, cyclodextrins (to cover site of active pharmaceutical compound subjected to oxidation), and carotenoids. For certain embodiments, the antioxidant that is not added is butylated hydroxyanisole (BHA), butylated hydroxytoluene (BHT), propyl gallate, ascorbic acid and esters thereof, e.g., ascorbyl palmitate, tocopherol and esters thereof, e.g., tocopherol acetate, including isomers thereof, e.g., alpha-tocopherol, or a combination thereof.

As described above, the stable transdermal adhesive composition is prepared by providing a polymerization reaction product of at least two ethylenically unsaturated monomers; and wherein the polymerization reaction product is dissolved and/or dispersed in a first liquid; separating at least a portion of the polymerization reaction product from the first liquid to provide a first washed polymerization reaction product; dissolving or dispersing the first washed polymerization reaction product in a second liquid; separating at least a portion of the first washed polymerization reaction product from the second liquid to provide a second washed polymerization reaction product; wherein the at least two ethylenically unsaturated monomers, if present in the second washed polymerization reaction product, are present at a level of less than 200 ppm of total unreacted monomer, based upon the total weight of the second washed polymerization reaction product; and combining the second washed polymerization reaction product with at least one pharmaceutically active compound which is susceptible to oxidative degradation to form a stable transdermal adhesive composition. In some instances, depending upon the pharmaceutically active compound to be used, one or more additional washing steps may be included for increased stability of the active. Accordingly, for certain of these embodiments, the method further comprises dissolving or dispersing the second washed polymerization reaction product in a third liquid; separating at least a portion of the second washed polymerization reaction product from the third liquid to provide a third washed polymerization reaction product; and combining the third washed polymerization reaction product instead of the second washed polymerization reaction product with the at least one pharmaceutically active compound which is susceptible to oxidative degradation to form the stable transdermal adhesive composition. Here, the at least two ethylenically unsaturated monomers, if present in the third washed polymerization reaction product, are present at a level of less than 200 ppm of total unreacted monomer, based upon the total weight of the third washed polymerization reaction product.

For certain embodiments, preferably the polymerization reaction product is dissolved and then precipitated out by adding a wash liquid which is a poor solvent for polymer included in the polymerization reaction product. A more thorough washing of the polymerization reaction product is thereby provided as compared with simply dispersing the polymerization reaction product in a wash liquid and then conducting the separation step. Accordingly, for certain embodiments, including any one of the above method embodiments, the separating, in each instance, is carried out by adding a wash liquid to the dissolved polymerization reaction product, allowing polymerization reaction product to precipitate, and separating the precipitated from the liquid (combination of wash liquid and liquid in which the polymerization reaction product was dissolve), to provide washed polymerization reaction product.

Suitable wash liquids include any nonreactive liquid which is a poor solvent for the polymer and in which unreacted monomer and initiator have some solubility. Examples include methanol, isopropyl alcohol, methanol/water mixtures, isopropyl alcohol/water mixtures, and the like.

Suitable liquids (first, second, third, etc.) for dissolving the polymerization reaction product include organic solvents which dissolve the polymerization reaction product and which are miscible with the wash liquid. Examples include acetone, ethyl acetate, ethyl acetate/methanol mixtures, preferably with not more than 30% methanol, and the like. When dispersing (including not fully dissolving) the polymerization reaction product, the suitable liquids (first, second, third, etc.) may include the wash liquids described above, or alternatively, the suitable liquids may be the wash liquids.

For certain embodiments, including any one of the above method embodiments, the method further comprises polymerizing the at least two ethylenically unsaturated monomers dissolved in the first liquid to provide the polymerization reaction product dissolved and/or dispersed in the first liquid.

For certain embodiments, including any one of the above method embodiments, preferably the at least two ethylenically unsaturated monomers, if present in the washed polymerization reaction product combined with the at least one pharmaceutically active compound, are present at a level of less than 100 ppm, based upon the total weight of the washed polymerization reaction product. For certain of these embodiments the level is less than 50 ppm.

For certain embodiments, including any one of the above method embodiments, preferably any free radical initiator, if present in the washed polymerization reaction product combined with at least one pharmaceutically active compound, is present at a level of less than 20 ppm, based upon the total weight of the washed polymerization reaction product. For certain of these embodiments, preferably the level is less than 10 ppm, more preferably less than 5 ppm.

For certain embodiments, including any one of the above method embodiments, preferably an antioxidant is not added to the stable transdermal adhesive composition.

The transdermal adhesive compositions typically contain a therapeutically effective amount of the pharmaceutically active compound, for example, rivastigmine. This amount will vary according to the form of the drug used, such as a particular salt form, the particular condition to be treated, the amount of time the composition is allowed to remain in contact with the skin of the subject, and other factors known to those of skill in the art. Generally, the amount of drug present in the transdermal drug delivery composition will be about 0.1 to about 40 percent by weight, typically about 5.0 to about 25 percent by weight, and more typically about 10.0 to about 20.0 percent by weight based on the total weight of the composition.

The transdermal adhesive compositions may optionally contain additives, including, for example excipients, skin permeation enhances, and solubilizers. Suitable excipients include, for example, amine oxides, unsaturated fatty acids, isopropyl myristate, lauroglycol, α-terpineol, polyethylene glycol, sorbitan esters, lactic acid, and dimethylsulfoxide. In one embodiment, the excipient is a skin permeation enhancer. Permeation enhancers are desirable excipients for use in transdermal drug delivery, because the skin typically presents an effective barrier to passage of most drug molecules. Amine oxides, unsaturated fatty acids, α-terpineol, polyethylene glycol, and sorbitan monooleate are preferred permeation enhancers. Amine oxides and unsaturated fatty acids are particularly effective permeation enhancers. Amine oxides include, for example, lauramine oxide and 2-hexadecyldimethylamine oxide. Unsaturated fatty acids include, for example, oleic acid, linoleic acid, and linolenic acid. Oleic acid is a preferred unsaturated fatty acid. Sorbitan esters include, for example, sorbitan monooleate, sorbitan laurate, and sorbitan stearate. Sorbitan monooleate is a preferred sorbitan ester. Isopropyl myristate and lauroglycol are also suitable for use as permeation enhancers. The permeation enhancer should be present in an amount sufficient to allow permeation of a sufficient amount of the pharmaceutically active compound across the skin so as to have a desired therapeutic effect. The amount of permeation enhancer is typically less than about 40% by weight of the total composition and more typically less than about 30%. The permeation enhancers are dispersed, typically substantially uniformly, and more typically dissolved in the composition.

In another embodiment of the invention, the excipient is a solubilizer of the pharmaceutically active compound, or a pharmaceutically acceptable salt thereof. Solubilizers may be used both to increase the amount of total dissolved drug in the composition and/or to increase the solubility of drug in one or more layers of the skin. The solubility of the pharmaceutically active compound in the solubilizer is typically greater than the solubility of the pharmaceutically active compound in the pressure sensitive adhesive. The amount of solubilizer used will vary depending on the desired dosing levels and durations, but the amount of solubilizer is typically less than about 35% by weight of the total composition and more typically less than about 25%. The total combined amount of permeation enhancer and solubilizer in the composition is typically less than about 40% by weight of the total composition and more typically less than about 30%. The solubilizers are dispersed, preferably substantially uniformly, and more preferably dissolved in the composition.

The transdermal adhesive compositions may optionally contain other additives or excipients, such as plasticizers, crosslinking agents, and colorants. Optional additives are dispersed, preferably substantially uniformly, and more preferably dissolved in the composition.

Transdermal drug delivery devices can be made using the transdermal adhesive compositions described above (including those made by the above methods) by coating a backing sheet with the transdermal adhesive composition, wherein the transdermal adhesive composition coating covers at least a portion of a major surface of the backing sheet.

Transdermal drug delivery devices that include compositions of the invention can be made in the form of an article such as a tape, a patch, a sheet, a dressing or any other form known to those skilled in the art. Generally, the device will be in the form of a patch of a size suitable to deliver a selected amount of drug through the skin.

For certain embodiments, including any one of the above device embodiments, the device will have a surface area of at least 1 $cm^2$ or at least 5 $cm^2$, and not more than 100 $cm^2$ or not more than 40 $cm^2$.

The devices can include a release liner that covers and protects the skin-contacting surface, e.g., the transdermal adhesive composition, prior to application to a subject. Suitable release liners include, but are not limited to, conventional release liners comprising a known sheet material, such as a polyester web, a polyethylene web, a polypropylene web, or a polyethylene-coated paper coated with a suitable fluoropolymer or silicone based coating. The devices can be packaged individually in a foil-lined pouch for storage, and may alternatively be provided in a rolled or stacked form suitable for use with a dispensing apparatus.

Examples of flexible backing materials employed as conventional tape backings that can be use as the backing sheet. Examples include those made from polymer films such as polypropylene; polyethylene, particularly low density polyethylene, linear low density polyethylene, metallocene polyethylenes, and high density polyethylene; polyvinyl chloride; polyester (e.g., polyethylene terephthalate); ethylene-vinyl acetate copolymer; polyurethane; cellulose acetate; and ethyl cellulose. Backings that are layered, such as polyethylene terephthalate-aluminum-polyethylene composites, are also suitable. Fabrics and non-wovens are likewise suitable. In one implementation, the backing is a continuous polymeric film that prevents ingress of external moisture into the transdermal adhesive composition, for example, from high ambient humidity and/or activities such as showering and bathing. Examples of such continuous films include, but are not limited to, polyurethane, polyethylene, and polyester.

The backing thickness is typically more than 10 μm, more typically more than 20 μm, and most preferably more than 40 μm. The backing thickness is typically less than 150 μm, more typically less than 125 μm, and most preferably less than 100 μm.

The transdermal adhesive composition can be prepared by combining the adhesive (washed polymerization reaction product optionally combined with a tackifier and/or other adhesive component), pharmaceutically active compound, and optional additives such as a permeation enhancer and/or solubilizers, with an organic solvent (e.g., ethyl acetate, isopropanol, methanol, acetone, 2-butanone, ethanol, toluene, alkanes, and mixtures thereof) to provide a coating composition. The mixture is shaken or stirred until a homogeneous coating composition is obtained. The resulting composition is then applied to a release liner using conventional coating methods (e.g., knife coating or extrusion die coating) to provide a predetermined uniform thickness of coating composition. Non-continuous or discontinuous coatings may be prepared using methods such as stripe coating, screen-printing, and ink jet printing.

The transdermal adhesive compositions and devices provided herein can be used to treat conditions for which the pharmaceutically active compound susceptible to oxidative degradation has been found to be effective. These treatments generally involve a method of delivering the pharmaceutically active compound to a mammal comprising the steps of: providing a transdermal adhesive composition according to any one of above composition or method embodiments or providing a device according to any one of the above device embodiments or method of making a device embodiments; positioning the transdermal adhesive composition on the skin of the mammal; and allowing the composition to remain on the skin for a time sufficient to permit systemic delivery of the pharmaceutically active compound and/or achieve the desired therapeutic result. The period of time for such treatment can be between about 6 hours and about 14 days, typically between about 1 day and about 7 days, and more typically between about 1 day and about 4 days.

The following examples are provided to more particularly illustrate various embodiments of the present invention, but the particular materials and amounts thereof recited in these examples, as well as other conditions and details are in no way intended to be limit this invention.

EXAMPLES

Materials
Preparation of the Copolymers

The copolymers used in the examples that follow were prepared generally according to the methods described below. The inherent viscosity values which are reported below were measured by conventional means using a Cannon-Fenske #50 viscometer in a water bath controlled at 27° C. to measure the flow time of 10 millimeters of the polymer solution (0.15 g of polymer per deciliter of ethyl acetate). The test procedure and apparatus are described in detail in *Textbook of Polymer Science*, F. W. Billmeyer, Wiley Interscience, Second Edition (1971), pages 84 and 85.

Copolymer A. Preparation of Isooctyl
Acrylate/Acrylamide/Vinyl Acetate (75/5/20)
Copolymer Isooctyl acrylate (IOA) (75 g), acrylamide (ACM) (5 g), vinyl acetate (VOAc) (20 g), ethyl acetate (136.5 g), and methanol (13.5 g) were added to a 1 quart vessel and the vessel was purged with nitrogen (2 minutes, 1.5 liters per minute nitrogen flow). 2,2'-azobis(2,4-dimethylvaleronitrile) (0.05 g) was added and the reaction was agitated at 42° C. for 6 hours. An additional portion of 2,2'-azobis(2,4-dimethylvaleronitrile) (0.05 g) was added and the vessel was again purged with nitrogen (2 minutes, 1.5 liters per minute nitrogen flow). The reaction was maintained at 42° C. for an additional 22 hours. The temperature was raised to 57° C. and the reaction was maintained an additional 6 hours. The resulting polymerization reaction product was diluted with ethyl acetate (30.6 g) and methanol (5 g). The percent solids of the resultant copolymer solution was 31 weight %. The measured inherent viscosity was 1.34 dL/g.

Copolymer B. Preparation of Solvent Washed
IsooctylAcrylate/Acrylamide/Vinyl Acetate
(75/5/20) Copolymer General Description of the Copolymer Solvent Washing Process:

A wash liquid, i.e., a non-solvent or poor solvent for the copolymer (for example, methanol) was added to a solution of copolymer adhesive, resulting in precipitation of the copolymer. The liquid phase was decanted, and the precipitated polymer was redissolved by the addition of solvent (for example, ethyl acetate). The washing process was repeated up to two more times (for total washing steps up to three times). The resulting solution was then concentrated by distillation. The effect of the washing steps was to remove substantial amounts of low molecular weight material from the original solution, providing a copolymer substantially free from impurities.

Detailed Description of the Copolymer Washing Process:

100 g of Copolymer A (75/5/20 IOA/ACM/VOAc, 31 weight % solids in 90/10 ethyl acetate/methanol, prepared as described above) was added to a clean vessel and methanol (200 g) was added without agitation. The mixture was then vigorously shaken using a mechanical shaker for 10 minutes to create a flocculate precipitate. The mixture was maintained without agitation for 2 hours. The precipitate settled to the bottom of the vessel as a gummy solid. The liquid was decanted from the vessel. An additional 50 g of ethyl acetate was added to the solid and the vessel was agitated for one hour (sample after first wash treatment). A second portion of methanol (200 g) was added without agitation. The mixture was then vigorously shaken using a mechanical shaker for 10 minutes to create a flocculate precipitate. The mixture was maintained without agitation for 2 hours. The precipitate settled to the bottom of the vessel as a gummy solid. The liquid was decanted from the vessel. An additional 50 g of ethyl acetate was added to the solid and the vessel was agitated for one hour (sample after second wash treatment). A third portion of methanol (200 g) was added without agitation. The mixture was then vigorously shaken using a mechanical shaker for 10 minutes to create a flocculate precipitate. The mixture was maintained without agitation for 2 hours. The precipitate settled to the bottom of the vessel as a gummy solid. The hazy liquid was decanted from the vessel. The resulting washed polymerization reaction product was dissolved in 50 mL of ethyl acetate and distilled under vacuum at 120° F. (49° C.) to provide a copolymer solution at 32 weight % solids in ethyl acetate/methanol (Copolymer B, sample after third wash treatment). The measured inherent viscosity was 1.45 dL/g.

Example 1

Copolymer A and samples of Copolymer A after one, two, and three (above Copolymer B) wash treatments were analyzed for residual monomers and the free radical initiator by gas chromatography using an HP-6850 gas chromatograph equipped with a split/splitless injection port and flame ionization detector (Hewlett Packard, Palo Alto, Calif.). The analytical column used was a DB-1 J&W 125-1035 capillary column (Agilent Technologies, Santa Clara, Calif.). The injection port was set to 250° C. and the flame ionization detector was set to 300° C. The oven temperature was set to 100° C. and the temperature was increased at a rate of 20° C./minute to a final oven temperature of 200° C. The compounds of interest were quantified by comparing peak integration values to a tetradecane internal standard. The concentration of the following compounds was determined in parts-per-million (ppm): acrylamide (ACM), isooctyl acrylate (IOA), 2,2'-azobis(2,4-dimethylvaleronitrile) (ABVN), isooctyl alcohol (IOOH), and isooctyl acetate (IOAc). The minimum detection limit (MDL) for ACM and ABVN was 8 ppm. The BDL for IOA, IOOH and IOAc was 26 ppm. The designation BDL refers to Below Detection Limit. Samples for analysis were prepared by precipitating a sample of the copolymer solution with methanol. A sample from the methanol phase was then injected into the gas chromatograph. The analysis for residual monomer and initiator, as well as IOOH and IOAc, in samples of Copolymer A, Copolymer B (sample after 3 wash procedures), and samples after one and two wash treatments is presented in Table 1.

TABLE 1

Concentration of Residual Monomers and Monomer Derived Impurities

| Sample | ACM (ppm) | IOA (ppm) | IOOH (ppm) | IOAc (ppm) |
| --- | --- | --- | --- | --- |
| Copolymer A | 222 | 779 | 2602 | 2016 |
| Sample after 1st wash treatment | 66 | 258 | 2313 | 590 |
| Sample after 2nd wash treatment | BDL | 37 | 1496 | 143 |
| Copolymer B (Sample after 3rd wash treatment) | BDL | BDL | 205 | BDL |

It is noted that because vinyl acetate is relatively volatile, essentially no vinyl acetate was expected in the copolymer adhesive of the devices described herein subsequent to device preparation. For this reason, analysis for vinyl acetate was not conducted in this Example. However, analysis for vinyl acetate in methanol extractions prepared as in Example 3 from devices made as in Example 2 showed that no detectable vinyl acetate was present.

Additional lots of Copolymer A and Copolymer B were prepared according to the procedure above and used to determine the concentration of the free radical initiator 2,2'-azobis(2,4-dimethylvaleronitrile) (ABVN) in each copolymer. The gas chromatography test method described above was used. The minimum detection limit (MDL) for ABVN was 8 ppm.

TABLE 2

Concentration of Initiator

| Sample | ABVN (ppm) |
| --- | --- |
| Copolymer A | 332 |
| Sample after 1st wash treatment | NT |
| Sample after 2nd wash treatment | NT |
| Copolymer B (Sample after 3rd wash treatment) | BDL |

NT = Not Tested

Example 2

A transdermal drug delivery (TDD) device using Copolymer A was prepared as follows. (S)—N-Ethyl-N-methyl-3-[1-(dimethylamino)ethyl]phenyl carbamate (1.8020 g) was added to a jar, followed by solvated Copolymer A ((32.6859 g) 25 weight % solids in a 25/75 Methanol/Ethyl Acetate solvent mixture). The solution was mixed on a shaker until a uniform mixture was obtained. The solution was coated using a knife set to deliver a wet thickness of 25 mil (0.025 inches or 0.635 mm) onto Loparex 5 CL PET 4400× release liner (available from Loparex Company, Cary, N.C.). The coated liner was then oven dried (for 12.5 minutes at 125° F. (52° C.)) and laminated onto a ScotchPak 9732 backing (available from 3M Company, St. Paul, Minn.). The resulting adhesive coating contained 18 weight % of (S)—N-ethyl-N-methyl-3-[1-(dimethylamino)ethyl]phenyl carbamate. The TDD devices were configured as circles with surface areas of 1, 5 or 10 cm².

TDD devices prepared with Copolymer A were analyzed for residual monomers and initiator by gas chromatography using an HP-6890 gas chromatograph equipped with a split/splitless injection port and flame ionization detector (Hewlett Packard, Palo Alto, Calif.). The analytical column used was a Rtx-Volatiles (30 meters, 0.32 mm ID, 1.5 micron) capillary column (Restek, Bellefonte, Pa.). The injection port was set to 270° C. and the flame ionization detector was set to 290° C. The oven temperature was set to 60° C. and the temperature was increased at a rate of 10° C./minute to a final oven temperature of 280° C. The compounds of interest were quantified by comparing peak integration values to an ethyl laurate internal standard. The concentration of the following compounds was determined in parts-per-million (ppm): acrylamide (ACM), isooctyl acrylate (IOA), and 2,2'-azobis(2,4-dimethylvaleronitrile) (ABVN). The minimum detection limit (MDL) for ACM was 12 ppm. The MDL for IOA was 11 ppm. The MDL for ABVN was 14 ppm. The designation BDL refers to Below Detection Limit. The liner was removed from a TDD device and the backing and coating were extracted using methanol. A sample from the methanol phase was then injected into the gas chromatograph. A total of three TDD devices were sampled and the results are presented as the average from the three samples.

TDD devices prepared with Copolymer A were analyzed for vinyl acetate (VOAc) by gas chromatography using an HP-6890 gas chromatograph equipped with a split/splitless injection port and flame ionization detector (Hewlett Packard, Palo Alto, Calif.). The analytical column used was a Rtx-1701 (30 meters, 0.32 mm ID, 1.0 micron) capillary column (Restek, Bellefonte, Pa.). The injection port was set to 220° C. and the flame ionization detector was set to 280° C. The oven temperature was set to 40° C. and the temperature was increased at a rate of 35° C./minute to a final oven temperature of 280° C. The concentration of vinyl acetate was quantified by comparing peak integration values to an acetonitrile internal standard. The concentration of vinyl acetate (VOAc) was determined in parts-per-million (ppm). The minimum detection limit (MDL) for VOAc was 42 ppm. The designation BDL refers to Below Detection Limit. A total of three TDD devices were sampled and the results are presented as the average from the three samples. The results are shown in Table 3

TABLE 3

Concentrations of Monomers and Initiator in TDD Devices with Copolymer A

| Description | IOA (ppm) | ACM (ppm) | VOAc (ppm) | ABVN (ppm) |
|---|---|---|---|---|
| Example 2 (Copolymer A) | 242 | 92 | BDL | 312 |

Example 3

The exact same procedure and analytical test methods as described in Example 2 was used to prepare and analyze TDD devices containing solvated Copolymer B, except that Copolymer B was used instead of Copolymer A. The results are shown in Table 4.

TABLE 4

Concentrations of Monomers and Initiator in TDD Devices with Copolymer B

| Description | IOA (ppm) | ACM (ppm) | VOAc (ppm) | ABVN (ppm) |
|---|---|---|---|---|
| Example 3 (Copolymer B) | BDL | BDL | BDL | BDL |

Example 4

The TDD devices described in Examples 2 and 3 were sealed in pouches (BAREX™/aluminum/paper laminates) and stored under conditions of 60° C./ambient humidity. The TDD devices were tested for percent total impurities within 1 week after preparation and at preset storage times (1 month and 2 months after preparation) using the following test method.

The liner was removed from a TDD device and the TDD device was placed in a 40 mL vial. The backing and coating were extracted using 20 mL of methanol solvent. The sample was shaken overnight. An aliquot from the sample was analyzed for percent total impurities by high performance liquid chromatography using an Agilent 1100 liquid chromatograph equipped with an ultraviolet detector (Agilent Technologies, Santa Clara, Calif.). The analytical column used was an XBridge C18, 75×4.6 mm, 3.5 mcm particle size HPLC column (Waters Corporation, Milford, Mass.). Analytes were separated using reversed-phased gradient elution chromatography. A linear gradient from 10-90% acetonitrile over 30 minutes was used at a flow rate of 1 mL/min. The compounds of interest were quantified by comparing peak integration values to an (S)—N-ethyl-N-methyl-3[1-(dimethylamino)ethyl]phenyl carbamate reference standard and the sum of these compounds are presented in Table 5 as percent total impurities. At each time point a total of three TDD devices were sampled and the results are presented as the average from the three samples.

TABLE 5

TDD Devices from Examples 2 and 3 Stored at 60° C. and Ambient Humidity

| | Percent Total Impurities | | |
|---|---|---|---|
| Description | Initial | 1 month | 2 months |
| TDD devices prepared with Copolymer A | 0.26 | 1.45 | 2.12 |
| TDD devices prepared with Copolymer B | 0.14 | 0.75 | 0.95 |

Example 5

A TDD device spiked with ABVN initiator was prepared as follows. (S)—N-Ethyl-N-methyl-3[1-(dimethylamino)ethyl]phenyl carbamate (1.7963 g) was added to a jar, followed by solvated Copolymer B ((32.5988 g) 25 weight % solids in a 25/75 Methanol/Ethyl Acetate solvent mixture). 2,2'-Azobis(2,4-dimethylvaleronitrile) (ABVN) (0.0015 g) was added last, and the solution was mixed on a shaker until a uniform mixture was obtained. The resulting solution was coated using a knife set to deliver a wet thickness of 25 mil (0.025 inches or 0.635 mm) onto Loparex 5 CL PET 4400× release liner (available from Loparex Company). The coated liner was then oven dried (for 12.5 minutes at 125° F.) and laminated onto a ScotchPak 9732 backing (available from 3M Company, St. Paul, Minn.). The resulting coating contained 18 weight % of (S)—N-ethyl-N-methyl-3-[1-(dimethylamino)ethyl]phenyl carbamate. The TDD devices were configured as circles with a surface area of 1, 5 or 10 cm$^2$.

Analysis for ABVN in the adhesive coating was conducted as in Example 2. The results are shown in Table 6.

TABLE 6

Concentration of ABVN Initiator in TDD Devices from Example 5

| Description | ABVN (ppm) |
|---|---|
| Example 5 | 230 |

Example 6

The TDD devices described in Example 5 were sealed in pouches (BAREX™/aluminum/paper laminates) and stored under conditions of 60° C./ambient humidity. The TDD devices were tested for percent total impurities within 1 week after preparation and after preset storage times (1 month and 2 months after preparation) as described in Example 4. The results are shown in Table 7.

TABLE 7

TDD Devices from Example 5 stored at 60° C. and Ambient Humidity

| | Total Percent Impurities | | |
|---|---|---|---|
| Description | Initial | 1 month | 2 months |
| TDD device prepared with Copolymer B and spiked with ABVN initiator (Example 5) | 0.27 | 1.20 | 1.67 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of delivering at least one pharmaceutically active compound to a subject, the method comprising contacting a transdermal adhesive composition with the subject, wherein the transdermal adhesive composition comprises:
    an adhesive comprising a washed polymerization reaction product of at least two ethylenically unsaturated monomers; and
    at least one pharmaceutically active compound which is susceptible to oxidative degradation;
    wherein the at least two ethylenically unsaturated monomers, if present in the adhesive as unreacted monomers, are present at a level of less than 200 ppm of total unreacted monomer, based upon the total weight of the adhesive;
    wherein any free radical initiator, if present in the adhesive, is present at a level of less than 20 ppm, based upon the total weight of the adhesive; and
    wherein the composition is essentially free of any added antioxidant.

2. A method of delivering at least one pharmaceutically active compound to a subject, the method comprising contacting a transdermal adhesive composition with the subject, wherein the transdermal adhesive composition comprises
    an adhesive comprising washed polymerization reaction product of at least two ethylenically unsaturated monomers;
    (S)—N-ethyl-N-methyl-3-[1-(dimethylamino)ethyl]phenyl carbamate or a pharmaceutically acceptable salt thereof;
    wherein the at least two ethylenically unsaturated monomers, if present in the adhesive as unreacted monomers, are present at a level of less than 200 ppm of total unreacted monomer, based upon the total weight of the adhesive; and
    wherein the composition is essentially free of any added antioxidant.

3. The method of claim 1, wherein the at least two ethylenically unsaturated monomers, if present in the adhesive, are present at a level of less than 100 ppm of total unreacted monomer.

4. The method of claim 1, wherein the at least two ethylenically unsaturated monomers comprise an ethylenically unsaturated group selected from the group consisting of acryloyl, methacryloyl, vinyl, and a combination thereof.

5. The method of claim 1, wherein the adhesive comprises the copolymerization product of at least one first monomer selected from the group consisting $C_4$ to $C_{12}$ alkyl acrylate monomers, $C_4$ to $C_{12}$ alkyl methacrylate monomers, and combinations thereof and at least one second monomer selected from the group consisting of acrylamide, N,N-diethylacrylamide, methacrylamide, vinyl acetate, vinyl alcohol, N-vinyl-2-pyrrolidone, 2-hydroxyethyl acrylate, 2-hydroxyethyl methacrylate, hydroxypropyl acrylate, glyceryl acrylate, 2-ethoxyethyl acrylate, 2-ethoxyethoxyethyl acrylate, tetrahydrofurfuryl acrylate, acrylic acid, methacrylic acid, pyrrolidonylethyl acrylate, 2-carboxyethyl acrylate, and combinations thereof.

6. The method of claim 5, wherein the at least one first monomer is selected from the group consisting of isooctyl acrylate, 2-ethylhexyl acrylate, cyclohexyl acrylate, 2-methylbutyl acrylate, butyl acrylate, and combinations thereof.

7. The method of claim 1, wherein the adhesive comprises the co-polymerization product of isooctyl acrylate, acrylamide, and vinyl acetate.

8. The method of claim 1, wherein the pharmaceutically active compound includes at least one group selected from the group consisting of tertiary amino, secondary amino, benzylic hydrogen-containing group, and combinations thereof.

9. The method of claim 1, wherein the pharmaceutically active compound is selected from the group consisting of: rivastigmine ((S)—N-ethyl-N-methyl-3-[1-(dimethylamino)ethyl]phenyl carbamate), buprenorphine, etidocaine, ropivacaine, clonidine, lidocaine, letrozole, fentanyl, indapamide, apomorphine, propylnorapomorphine, salbutamol, lisuride, dihydroergotamine, pergolide, terguride, proterguride, propranolol, imipramine, guanethidine, cyproheptadine and a pharmaceutically acceptable salt of any one of the preceding compounds.

10. The method of claim 9, wherein the pharmaceutically active compound is (S)—N-ethyl-N-methyl-3-[1-(dimethylamino)ethyl]phenyl carbamate or a pharmaceutically acceptable salt thereof.

11. A method of delivering at least one pharmaceutically active agent to a subject, the method comprising contacting the subject with a transdermal drug delivery device comprising:
    a transdermal adhesive composition comprising:
        an adhesive comprising a washed polymerization reaction product of at least two ethylenically unsaturated monomers; and
        at least one pharmaceutically active compound which is susceptible to oxidative degradation;
        wherein the at least two ethylenically unsaturated monomers, if present in the adhesive as unreacted monomers, are present at a level of less than 200 ppm of total unreacted monomer, based upon the total weight of the adhesive;
    a backing sheet coated with the transdermal adhesive composition, wherein the transdermal adhesive composition coating covers at least a portion of a major surface of the backing sheet; and
    wherein the composition is essentially free of any added antioxidant.

12. The method of claim 10, wherein the at least two ethylenically unsaturated monomers, if present in the adhesive, are present at a level of less than 100 ppm of total unreacted monomer.

13. The method of claim 11, wherein any free radical initiator, if present in the adhesive, is present at a level of less than 20 ppm, based upon the total weight of the adhesive.

14. The method of claim 11, wherein the at least two ethylenically unsaturated monomers comprise an ethylenically unsaturated group selected from the group consisting of acryloyl, methacryloyl, vinyl, and a combination thereof.

15. The method of claim 11, wherein the adhesive comprises the copolymerization product of at least one first monomer selected from the group consisting $C_4$ to $C_{12}$ alkyl acrylate monomers, $C_4$ to $C_{12}$ alkyl methacrylate monomers, and combinations thereof and at least one second monomer selected from the group consisting of acrylamide, N,N-diethylacrylamide, methacrylamide, vinyl acetate, vinyl alcohol, N-vinyl-2-pyrrolidone, 2-hydroxyethyl acrylate, 2-hydroxyethyl methacrylate, hydroxpropyl acrylate, glyceryl acrylate, 2-ethoxyethyl acrylate, 2-ethoxyethoxyethyl acrylate, tetrahydrofurfuryl acrylate, acrylic acid, methacrylic acid, pyrrolidonylethyl acrylate, 2-carboxyethyl acrylate, and combinations thereof.

16. The method of claim 15, wherein the at least one first monomer is selected from the group consisting of isooctyl acrylate, 2-ethylhexyl acrylate, cyclohexyl acrylate, 2-methylbutyl acrylate, butyl acrylate, and combinations thereof.

17. The method of claim 11, wherein the adhesive comprises the co-polymerization product of isooctyl acrylate, acrylamide, and vinyl acetate.

18. The method of claim 11, wherein the pharmaceutically active compound includes at least one group selected from the group consisting of tertiary amino, secondary amino, benzylic hydrogen-containing group, and combinations thereof.

19. The method of claim 11, wherein the pharmaceutically active compound is selected from the group consisting of: rivastigmine ((S)—N-ethyl-N-methyl-3-[1-(dimethylamino)ethyl]phenyl carbamate), buprenorphine, etidocaine, ropivacaine, clonidine, lidocaine, letrozole, fentanyl, indapamide, apomorphine, propylnorapomorphine, salbutamol, lisuride, dihydroergotamine, pergolide, terguride, proterguride, propranolol, imipramine, guanethidine, cyproheptadine and a pharmaceutically acceptable salt of any one of the preceding compounds.

20. The method of claim 11, wherein the pharmaceutically active compound is (S)—N-ethyl-N-methyl-3-[1-(dimethylamino)ethyl]phenyl carbamate or a pharmaceutically acceptable salt thereof.

21. A method of making a transdermal adhesive composition, the method comprising:
  washing the polymerization reaction product of at least two ethylenically unsaturated monomers to form a washed polymerization reaction product and admixing the washed polymerization reaction product with at least one pharmaceutically active compound which is susceptible to oxidative degradation;
  wherein the transdermal adhesive composition comprises:
  the adhesive comprising a washed polymerization reaction product of at least two ethylenically unsaturated monomers; and
  the least one pharmaceutically active compound which is susceptible to oxidative degradation;
  wherein the at least two ethylenically unsaturated monomers, if present in the adhesive as unreacted monomers, are present at a level of less than 200 ppm of total unreacted monomer, based upon the total weight of the adhesive;
  wherein any free radical initiator, if present in the adhesive, is present at a level of less than 20 ppm, based upon the total weight of the adhesive; and
  wherein the composition is essentially free of any added antioxidant.

* * * * *